United States Patent
Jones et al.

(10) Patent No.: US 8,206,413 B2
(45) Date of Patent: *Jun. 26, 2012

(54) CHEMICALLY BASED VASCULAR OCCLUSION DEVICE DEPLOYMENT

(75) Inventors: Donald K. Jones, Austin, TX (US); Vladimir Mitelberg, Austin, TX (US)

(73) Assignee: Codman & Shurtleff, Inc., Raynham, MA (US)

( * ) Notice: Subject to any disclaimer, the term of this patent is extended or adjusted under 35 U.S.C. 154(b) by 113 days.

This patent is subject to a terminal disclaimer.

(21) Appl. No.: 12/839,143

(22) Filed: Jul. 19, 2010

(65) Prior Publication Data

US 2010/0286723 A1 Nov. 11, 2010

Related U.S. Application Data

(62) Division of application No. 11/171,897, filed on Jun. 30, 2005, now Pat. No. 7,780,695.

(51) Int. Cl.
*A61M 29/00* (2006.01)
(52) U.S. Cl. ............... 606/200; 604/90; 604/201
(58) Field of Classification Search ............ 606/108, 606/200, 142, 191, 213; 623/1.1, 1.23, 23.72; 604/90, 201; 92/89–93; 124/63, 65, 56
See application file for complete search history.

(56) References Cited

U.S. PATENT DOCUMENTS

| | | |
|---|---|---|
| 5,108,407 A | 4/1992 | Geremia et al. |
| 5,188,614 A | 2/1993 | Hart |
| 5,378,233 A | 1/1995 | Haber et al. |
| 5,478,323 A | 12/1995 | Westwood et al. |
| 5,599,312 A | 2/1997 | Higashikawa |
| 5,609,608 A | 3/1997 | Benett et al. |
| 5,637,087 A | 6/1997 | O'Neil et al. |
| 5,669,880 A | 9/1997 | Solar |
| 5,750,585 A | 5/1998 | Park et al. |
| 5,989,242 A | 11/1999 | Saadat et al. |
| 6,056,759 A | 5/2000 | Fiedler |
| 6,063,100 A | 5/2000 | Diaz et al. |
| 6,068,644 A | 5/2000 | Lulo et al. |
| 6,117,142 A | 9/2000 | Goodson et al. |
| 6,238,415 B1 | 5/2001 | Sepetka et al. |
| 6,361,547 B1 | 3/2002 | Hieshima |
| 6,398,761 B1 | 6/2002 | Bills et al. |
| 6,419,656 B1 | 7/2002 | Vetter et al. |

(Continued)

FOREIGN PATENT DOCUMENTS

EP 0992219 4/2000

(Continued)

OTHER PUBLICATIONS

Translation of JP07116262.*

(Continued)

*Primary Examiner* — Gary Jackson
*Assistant Examiner* — Erin Colello
(74) *Attorney, Agent, or Firm* — Cook Alex Ltd.

(57) ABSTRACT

A vascular occlusion device deployment system for placing an occlusion device at a preselected site within the vasculature of a patient. The deployment system employing a pusher having a lumen with an opening at the distal end of the pusher. A vascular occlusion device is connected to the distal end of the pusher by a portion that is removeably disposed within the opening. The portion of the occlusion device is forced out of the opening by an expandable reaction chamber, thereby deploying the occlusion device.

5 Claims, 2 Drawing Sheets

U.S. PATENT DOCUMENTS

| | | |
|---|---|---|
| 6,428,557 B1 | 8/2002 | Hilaire |
| 6,478,773 B1 | 11/2002 | Gandhi et al. |
| 6,494,884 B2 | 12/2002 | Gifford et al. |
| 6,544,225 B1 | 4/2003 | Lulo et al. |
| 6,554,849 B1 | 4/2003 | Jones et al. |
| 6,641,576 B1 | 11/2003 | Vito et al. |
| 6,689,141 B2 | 2/2004 | Ferrera et al. |
| 6,743,236 B2 | 6/2004 | Barry et al. |
| 6,871,594 B1 | 3/2005 | Estrella |
| 6,896,842 B1 | 5/2005 | Hamilton et al. |
| 6,958,068 B2 | 10/2005 | Hieshima |
| 6,981,963 B2 | 1/2006 | Barker et al. |
| 6,994,711 B2 | 2/2006 | Hieshima et al. |
| 7,357,809 B2 | 4/2008 | Jones et al. |
| 2001/0002438 A1 | 5/2001 | Sepetka et al. |
| 2002/0077589 A1 | 6/2002 | Tessari |
| 2003/0093094 A1 | 5/2003 | Diaz et al. |
| 2003/0220666 A1 | 11/2003 | Mirigian et al. |
| 2004/0153025 A1 | 8/2004 | Seifert et al. |
| 2004/0218966 A1 | 11/2004 | Fuller |
| 2004/0225279 A1 | 11/2004 | Raymond |
| 2005/0131454 A1 | 6/2005 | Hieshima |
| 2005/0131455 A1 | 6/2005 | Hieshima et al. |
| 2007/0239192 A1 | 10/2007 | Lizenberg et al. |
| 2007/0270930 A1 | 11/2007 | Schenck |

FOREIGN PATENT DOCUMENTS

| | | |
|---|---|---|
| EP | 1537838 | 6/2005 |
| JP | 07116262 A | 9/1995 |
| WO | WO 92/09651 | 6/1992 |
| WO | WO 02/32326 A2 | 4/2002 |
| WO | WO 2004062461 | 7/2004 |

OTHER PUBLICATIONS

Notification of Reasons for Refusal (Translation, Oct. 4, 2011) in companion Japanese Patent Appln. 2006-180032.

European Search Report in EP06253238 dated Oct. 24, 2006.

* cited by examiner

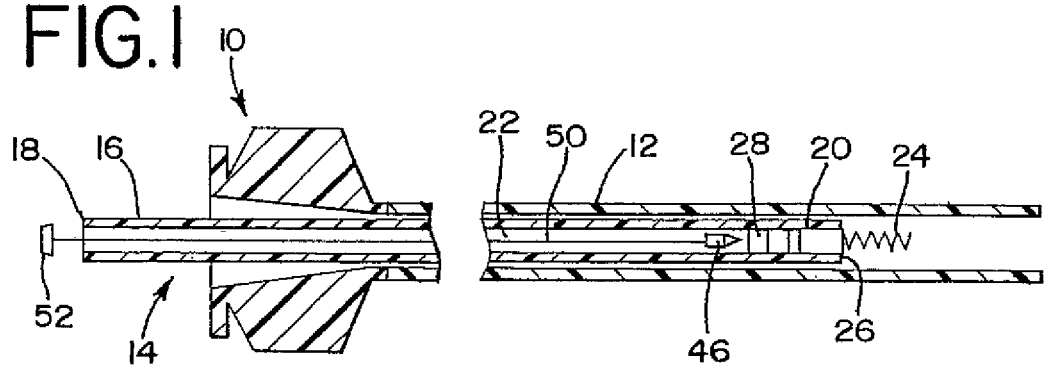
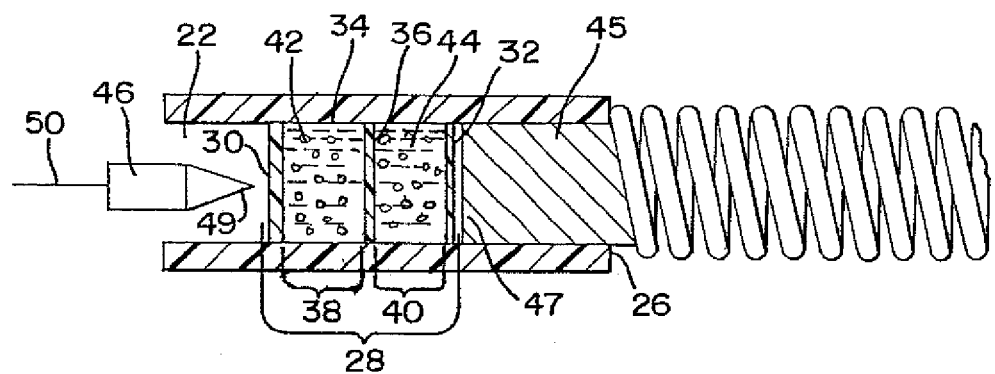
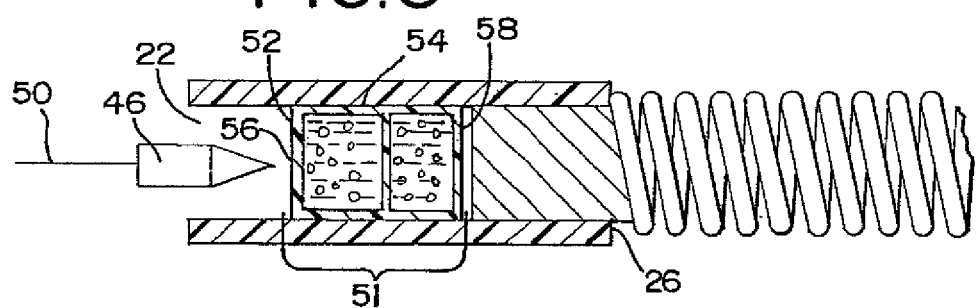
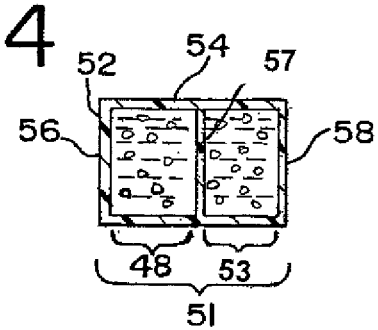

CHEMICALLY BASED VASCULAR OCCLUSION DEVICE DEPLOYMENT

This application is a divisional of U.S. application Ser. No. 11/171,897, filed Jun. 30, 2005, now U.S. Pat. No. 7,780,695, hereby incorporated by reference hereinto.

FIELD OF THE INVENTION

The present invention is related to deployment systems and methods for accurately and rapidly deploying vascular occlusion devices at a preselected location within the vascular system of a patient, and more particularly, deployment approaches that utilize an expanding chemical reaction chamber to facilitate rapid deployment of vascular occlusion devices.

BACKGROUND OF THE INVENTION

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat such a defect. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the coil through the catheter and out of the distal end of the catheter into the delivery site. Some of the problems that have been associated with these procedures relate to the accuracy of coil placement. For example, the force of the coil exiting the delivery catheter may cause the coil to over shoot the predetermined site or dislodge previously deployed coils. Also, once the coil is pushed out of the distal end of the catheter, the coil cannot be retracted and may migrate to an undesired location. Often, retrieving and repositioning the coil requires a separate procedure and has the potential to expose the patient to additional risk.

In response to the above mentioned concerns, numerous devices and release mechanisms have been developed in an attempt to provide a deployment system which allows control of the occlusion device after the device has been delivered by the catheter and provides a rapid release or detachment mechanism to release the device once it is in place. One such device is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber. One drawback is that connecting the resistance heating coil to the power source requires running multiple wires through the pusher member. Additionally, the electrical current traveling through the wires may create stray electromagnetic fields that interfere with other surgical and monitoring equipment.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transmits the light into heat energy. The heat energy raises the temperature of the connector and opens the fingers, thereby releasing the embolic coil. This type of ball and socket connection is rigid and causes the catheter to be stiff, making it difficult to guide the catheter through the vasculature of the body. This patent, and all other patents and references identified herein are hereby incorporated herein by reference.

Further, all of the above-identified delivery systems require electronic equipment powered by a power source. If the electronic equipment is defective or the power source fails, for example a battery pack fails, the procedure may be prolonged while the equipment is repaired or replaced. Prolonging the procedure may expose the patient to additional risk.

Therefore, a need remains for a rapid release vascular occlusion deployment system or method that does not rely on electrical equipment or a power supply, is simple to manufacture, flexible and easy to guide through the vasculature of the body, provides better control over the occlusion device, and reduces the possibility of interference with other surgical and/or monitoring equipment.

SUMMARY OF INVENTION

The present invention embodies a deployment system and method for accurately and rapidly deploying a vascular occlusion device at a preselected site within the vasculature of a patient. The deployment system may employ an elongated flexible delivery catheter for guiding a deployment unit to the preselected site. The deployment unit includes a delivery tube or pusher that pushes and guides the vascular occlusion device, such as an embolic coil, through the delivery catheter to the preselected site.

The pusher may include an internal lumen which has an opening at the distal end of the pusher. The occlusion device includes a portion, such as a headpiece, which is removeably disposed within the opening by a friction fit between the headpiece and the inner surface of the pusher. This arrangement maintains the connection between the occlusion device and the deployment unit until the desired deployment.

A reaction chamber is positioned with the lumen of the pusher. The reaction chamber includes an expandable wall adjacent the headpiece of the occlusion device. Two reactants are mixed within the chamber to create a product that expands to a volume greater than the original reactants. The product pushes against the expandable wall of the chamber which in turn contacts the headpiece. The force of the expandable wall against the headpiece overcomes the fictional force between the headpiece and the inner wall of the lumen, forcing the headpiece out of the opening, thereby deploying the vascular occlusion device.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein:

FIG. 1 is an enlarged partially sectioned view of the vascular occlusion device deployment system of a preferred embodiment of the present invention;

FIG. 2 is an enlarged partially sectioned view showing the deployment unit of FIG. 1 prior to deployment of the occlusion device;

FIG. 3 is an enlarged partially sectioned view showing another embodiment of the deployment unit of the present invention;

FIG. 4 is a cross-sectional view of the reaction chamber of the deployment unit shown in FIG. 3.

DESCRIPTION OF THE PREFERRED EMBODIMENTS

Figure 5:
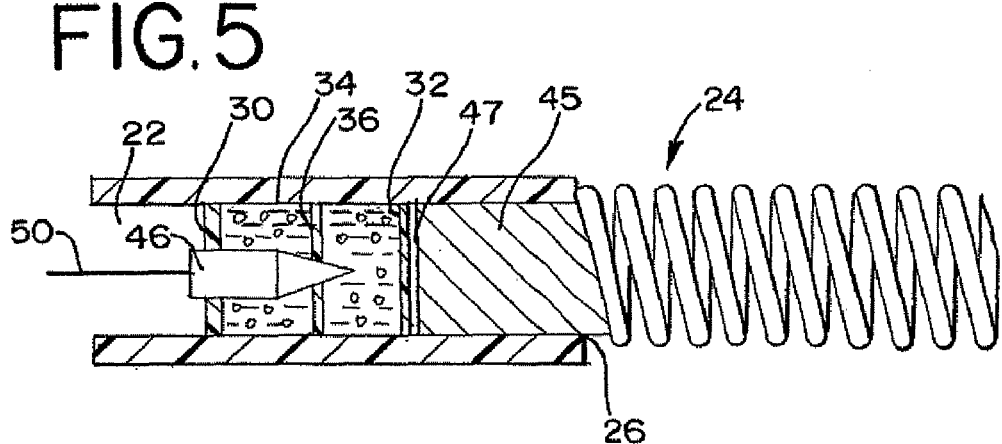
FIG. 5 is an enlarged partially sectioned view of deployment unit of FIG. 2 with the piercing element piercing the walls of the reaction chamber.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 generally illustrates a preferred embodiment of the vascular occlusion device deployment system of the present invention. The deployment system, generally designated at 10, includes an elongated flexible guiding catheter 12 which is inserted into the vasculature of a patient and used to guide a deployment unit, generally designed 14, to a preselected site in a manner generally known in the art. The deployment system 14 includes an elongated flexible pusher or delivery tube 16 having a proximal end portion 18 and a distal end portion 20. An internal lumen 22 extends from the proximal end portion 18 to the distal end portion 20 of the pusher 16. A vascular occlusion device 24, generally illustrated as an embolic coil, is removeably disposed within an opening 26 (which can be seen in FIG. 7) of the lumen 22 at the distal end 20 of the pusher 16.

The lumen 22 includes a reaction chamber 28 located proximal the opening 26 of the lumen. One embodiment of this reaction chamber 28 is illustrated in FIG. 2. In this embodiment, the reaction chamber is defined by a proximal wall 30, a distal wall 32 and an inner surface 34 of the pusher. The reaction chamber 28 typically has an axial length between about 3 millimeters and about 6 millimeters. An intermediate wall 36 is located between the proximal wall 30 and the distal wall 32 to divide the reaction chamber 28 into a first chamber 38 and a second chamber 40. Each of the chambers 38, 40 has an axial length preferably between about 1 millimeter and about 5 millimeters. The respective chambers need not have identical axial lengths.

The proximal wall 30 and the intermediate wall 36 are comprised of a piercable membrane. The distal wall 32 is comprised of an elastic expandable membrane. Preferably, the distal wall is a membrane made of a silicone elastomer having substantial flexibility and elasticity. The other membranes also can be made of a silicone polymer. The materials used in forming the proximal wall 30, distal wall 36 and intermediate wall 32 should be selected as not to significantly degrade while in contact with the reactant materials.

Typically, the respective membranes will have different Durometer hardness values. For example, the proximal wall 30 and the intermediate wall 36 preferably are made of a higher Durometer polymer than the distal wall 32. Further, the membranes or walls 30, 32 and 36 of this embodiment may be attached to the inner surface 34 of the pusher 16 by an adhesive, such as a silicone or cyanoacrylate adhesive, or by any other suitable manner.

A first reactant 42 is housed within the first chamber 38 and a second reactant 44 is housed within the second chamber 40. When the first and second reactants 42, 44 are mixed, they produce a product which has a greater volume than the combined volume of the first and second reactants prior to mixing. The first and second reactants 42, 44 can be any reactants that produce a product having a greater volume than the original compositions. Preferably, the first and second reactants may be any of the reactants disclosed in Cooke et al. WO 92/09651, hereby incorporated herein by reference, which produce a polycyanoacrylate foam. In particular, the first reactant is preferably a mixture of cyanoacrylate monomer and ethanol and the second reactant is preferably a mixture of ethanol and N,N-Dimethyl-p-toluidine. Other reactant materials, that when combined form a foam material with an increased bulk volume relative to the reactants, such as precursors for polyurethane foam are also suitable.

The delivery unit 14 also includes a piercing member 46, generally illustrated as a mandrel. As illustrated in FIGS. 1 and 2, the piercing member 46 includes a pointed tip 49 for piercing the proximal wall 30 and the intermediate wall 36. Illustratively, the piercing member 46 may be axially advanced and retracted through the lumen 22 by a control cable 50 that is attached to the proximal end of the piercing member 46. A control handle 52 may be connected to the proximal end of the cable 50 to facilitate such movement. Alternatively, the control cable 50 may take the form of a rod, wire or tubular member with sufficient flexibility and pushability to navigate through lumen 22, as well as, controllably advance piercing member 46.

The illustrated vascular occlusion device 24 includes a portion or headpiece 45 which is sized and shaped to be removeably disposed within the opening 26 at the distal end 20 of the pusher 16 so that a proximal end 47 of the headpiece 45 is adjacent the distal wall 32 of the chamber 28. The headpiece 45 is preferably held in place by a friction fit with the inner surface 34 of the pusher until the desired time of deployment, as will be discussed herein. Alternatively, the headpiece 45 may be held in place by a relatively weak biocompatible adhesive or by any other suitable manner.

As stated above, the occlusion device 24 may be an embolic coil which may take various forms and configurations, and may also be filled with a fibrous material or may be coated with a beneficial substance, such as a biogel to promote clotting. Alternatively, the occlusion device also may be any other occlusive device or approach known in the art such as hydrogels, foams, bioactive coils, braids, cables and hybrid devices.

A second embodiment of the delivery unit 14 is illustrated in FIGS. 3 and 4. This embodiment is similar to the first embodiment except that the reaction chamber 51 comprises a unit that is separate from the pusher member, as shown in FIG. 4 and positioned within the pusher member. Illustratively, the reaction chamber 51 comprises a cylindrical housing 52 having a sidewall 54, a proximal wall or membrane 56 and a distal wall or membrane 58. Similar to the first embodiment, the reaction chamber 51 is separated into two chambers 48, 53 by an intermediate wall or membrane 57. The proximal wall 56, the distal wall 58 and the intermediate wall 57 are preferably of the same material and construction as described above in the previous embodiment.

The reaction chamber 51 is located proximal to the opening 26 of the lumen 22 so that the distal wall 58 of the reaction chamber 51 is adjacent the proximal end 47 of the headpiece 45 of the occlusion device 24. As previously described, the materials used to form the reaction chamber should be relatively unaffected and not significantly degrade when in contact with the reactant materials. The chamber 51 may be held in place by an adhesive, such as a silicone or cyanoacrylate adhesive.

In operation, the catheter 12 is inserted into the vasculature of the patient and positioned at a preselected location, typically in conjunction with other devices and professional procedures as generally known in the art. The delivery unit 14 is inserted into the catheter 12, and once the desired location is reached, the delivery unit 14 is advanced and/or the catheter 12 is moved in a retrograde manner such that the delivery unit 12 moves with respect to and within the catheter until the occlusion device 24 moves through the catheter 12 and out of the distal end of the catheter. During the procedure and before the occlusion device 24 has been deployed, if it is determined that the distal end of the catheter 12 or the occlusion device 24 is not in the correct location, the occlusion device may be retrieved back into the distal end of the catheter by retracting the delivery unit 14 proximally or advancing the catheter distally. Once the occlusion device as been retrieved, the catheter and/or the occlusion device may be repositioned.

Figure 6:
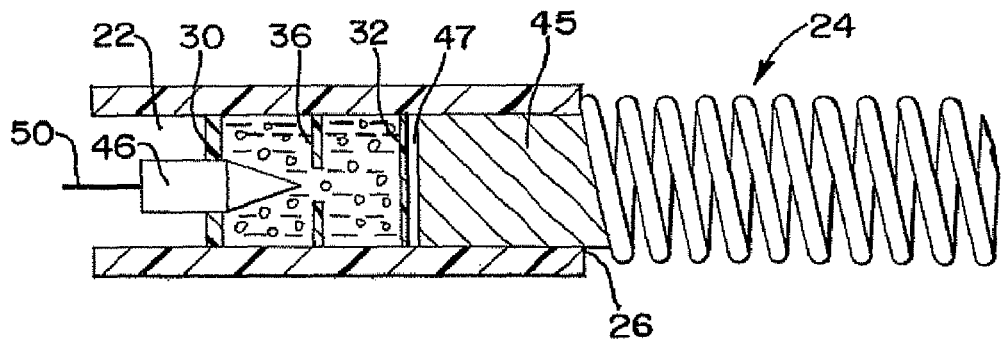
FIG. 6 is an enlarged partially sectioned view of deployment unit of FIG. 2 with the piercing element being retracted after piercing the intermediate wall.
Figure 7:
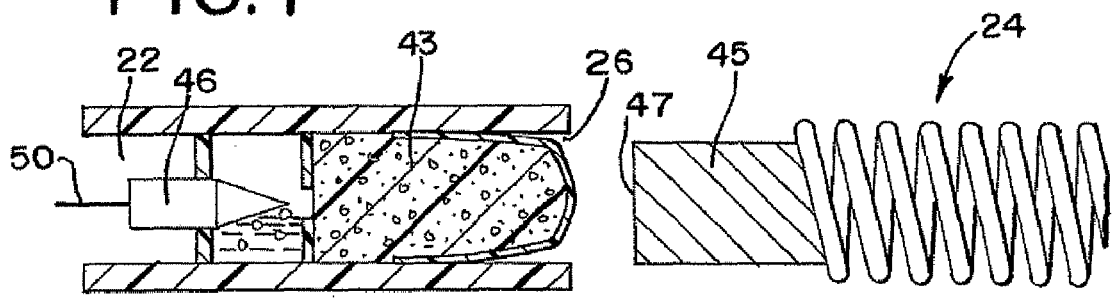
FIG. 7 is an enlarged partially sectioned view of the deployment unit of FIG. 2 shown just after deployment of the vascular occlusion device.

When the occlusion device 24 is in the correct position, the piercing member 46 may be advanced distally within the lumen 22 by manipulating the control handle 52 and cable 50. As illustrated in FIG. 5, the piercing member 46 is advanced until the tip 49 pierces the proximal membrane or wall 30 and the intermediate wall 36 of the chamber 28. As illustrated in FIG. 6, piercing member 46 is slightly retracted to allow the first reactant 42 and the second reactant 44 to mix. The proximal wall 30 is shown as a self-sealing wall which seals around the piercing element 46 after the piercing element has pierced the proximal wall so that the reactants are prevented from leaking out of the chamber 28. The first and second reactants 42, 44 mix to form a product 43 which has a greater volume than the first and second reactants. The expanding volume of the product 43 forces the lower durometer distal wall 32 of the reaction chamber to expand or stretch distally within the lumen, contacting the proximal end 47 of the headpiece 45 and forcing the headpiece 45 out of the opening 26, thereby deploying the occlusion device, as illustrated in FIG. 7.

Figure 8:
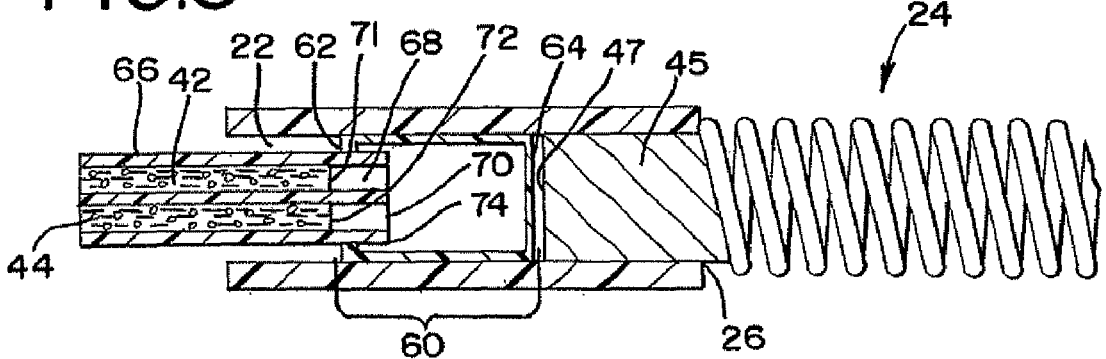
FIG. 8 is an enlarged partially sectioned view of another embodiment of the deployment unit of the present invention.

Another embodiment of the delivery unit 14 is illustrated in FIG. 8. Illustratively, the reaction chamber 60 is formed of a single unit and may be attached within the lumen 22 at a location and in a manner as described above. The reaction chamber 60 has a proximal wall 62 and a distal wall 64 which are comprised of polymers as described above. Alternatively, the reaction chamber 60 may be similar to that which is described in FIG. 2 in that a portion of the reaction chamber 28 is defined by the inner surface 34 of the pusher 16.

A dual-lumen dispending tube 66 extends into the reaction chamber 60 preferably through the proximal wall 62. The dual-lumen dispending tube 66 includes a first reactant 42 in a first lumen 68 and a second reactant 44 in a second lumen 70. Each lumen 68, 70 preferably is closed at a distal location by a breakable seal 71, 72. The first and second reactants 42, 44 are the same as described above in the previous embodiments and form a product which has a greater volume than the original compositions. The dual-lumen dispensing tube 66 is preferably plunger activated, but may also be activated by any other acceptable method known in the art.

In operation, the previously described procedure is employed to place the occlusion device 24 at a preselected site within the vasculature of the patient. Once the occlusion device 24 is at the desired location, the dispensing tube 66 is activated, and the first reactant 42 and the second reactant 44 are dispensed out the dispensing tube 66 into the reaction chamber 60. The reactants 42, 44 mix together and react to form a product which has a larger volume than the original reactants. As the product expands, the product stretches the lower Durometer and/or flexible distal wall 64 of the reaction chamber 60 toward the opening 26 of the pusher 16. The expanding distal wall 64 contacts the headpiece 45 of the occlusion device 24, and forces headpiece 45 out of the opening 26. Alternatively the dispensing tube 66 may include additional lumens of which one may serve as a vent lumen 74 to reaction chamber 60 to prevent the build up of fluid pressure within the reaction chamber when dispensing the reactants.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A method for deployment of a vascular occlusion device at a preselected location within the vasculature of a patient, comprising:

providing a deployment unit comprising a pusher member having a distal end opening and a chamber proximal thereof, the chamber having a flexible distal wall;

disposing a removable vascular occlusion device having a protruding portion into the distal end opening of the lumen;

using the deployment unit to place the vascular occlusion device at a preselected location within the vasculature of a patient;

causing at least a first reactant and a second reactant to react within the chamber, said reactants producing a product which has a larger volume than the reactants; and whereby the expanding product expands the flexible distal wall, without otherwise expanding the chamber, toward the distal end opening to remove the protruding portion from the distal end opening of the lumen, thereby deploying the vascular occlusion device.

2. The method according to claim 1, wherein said causing includes breaching a divider separating the first reactant and the second reactant.

3. The method according to claim 1, wherein said first reactant comprises a mixture of cyanoacrylate monomer and ethanol, and the second reactant comprises mixture of ethanol and N,N-Dimethyl-p-toluidine.

4. The method according to claim 1, wherein said causing includes dispensing the first and second reactants into the chamber.

5. The method according to claim 1 wherein said providing includes the chamber having a proximal wall that has a higher Durometer hardness than that of the flexible distal wall.

* * * * *